United States Patent [19]

Eilingsfeld et al.

[11] 4,117,019

[45] Sep. 26, 1978

[54] MANUFACTURE OF O-BENZYLTOLUENES

[75] Inventors: Heinz Eilingsfeld, Frankenthal; Manfred Patsch; Karl-Gerhard Baur, both of Ludwigshafen; Wolfgang Ruehenbeck, Weinheim, all of Fed. Rep. of Germany

[73] Assignee: BASF Aktiengesellschaft, Ludwigshafen, Fed. Rep. of Germany

[21] Appl. No.: 549,910

[22] Filed: Feb. 14, 1975

[30] Foreign Application Priority Data

Feb. 22, 1974 [DE] Fed. Rep. of Germany ....... 2408529
Jun. 11, 1974 [DE] Fed. Rep. of Germany ....... 2428197
Jun. 18, 1974 [DE] Fed. Rep. of Germany ....... 2429194
Nov. 30, 1974 [DE] Fed. Rep. of Germany ....... 2456747

[51] Int. Cl.$^2$ .................... C07C 25/18; C07C 15/16
[52] U.S. Cl. ............................ 260/649 R; 260/668 C
[58] Field of Search ...................... 260/649 R, 668 C

[56] References Cited

U.S. PATENT DOCUMENTS 2,981,765  4/1961  Fetterly ........................... 260/668 C Primary Examiner—C. Davis
Attorney, Agent, or Firm—Keil, Thompson & Shurtleff

[57] ABSTRACT

A process for the manufacture of o-benzyltoluenes by reaction of o-xylyl halides with benzenes in the presence of sulfuric acid or in the presence of phosphoric acid and adjuvants or in the presence of sulfuric acid and adjuvants. The products are starting materials for the manufacture of anthracene and anthraquinone and their derivatives.

13 Claims, No Drawings

MANUFACTURE OF O-BENZYLTOLUENES

The present invention relates to a process for the manufacture of o-benzyltoluenes by reaction of o-xylyl halides with benzenes in the presence of sulfuric acid or in the presence of phosphoric acid and adjuvants or in the presence of sulfuric acid and adjuvants.

o-Benzyltoluene is produced, alongside other products, on heating toluene with benzyl chloride in the presence of zinc dust (Chemische Berichte, 6, 906 et seq., (1873)) or of beryllium chloride (Chemische Berichte, 72, 1,414 et seq., (1939)). o-Benzyltoluene is also formed, in poor yield, when a mixture of o-xylyl chloride and benzene is treated with zince dust (Chemische Berichte, 7, 1,544 et seq., (1874)). All these processes are unsuitable for industrial use, since they either give poor yields or give mixtures which are difficult to separate. The hydrogenation of a o-benzoylbenzoic acid ethyl ester in the presence of copper chromite at 250° C also gives o-benzyltoluene (Journal of the American Chemical Society, 55, 1,669 et seq., (1933)). The manufacture of the catalyst, and in particular the multi-stage manufacture of the starting material, are involved and uneconomical, so that this process is also unsatisfactory, in industrial operation, in that it is not simple, economical and trouble-free.

Sulfuric acid has not hitherto been used in industrial alkylations with alkyl chlorides, since side reactions were to be expected. Thus, it was to be expected that alkyl chlorides would undergo hydrolysis to alcohols and that these would, at least to a certain extent, be converted to sulfuric acid esters, The possibility of sulfonation of the benzene nucleus also existed. Hence, to obtain individual alkylation products, the industrial process used was first to manufacture olefins from chloroparaffins by dehydrohalogenation; these olefins then underwent a clearly defined reaction with benzene (Erdol and Kohle, 20, 786 – 787 (1967)).

A factor which adds to the difficulty of the reaction of o-xylyl chloride with benzene and its derivatives is that o-xylyl chloride can very easily undergo sulfonation, and that low yields are therefore to be expected. Furthermore, it had to be assumed that xylyl halides would preferably react with themselves and only to a minor extent with benzenes. Thus an article in Comp. Rend., 250, 1,659 – 1,661 (1960) shows that the reaction of benzyl chloride with benzene in the presence of metal halides such as $SbCl_5$, $TiCl_4$ and $BiCl_3$ in aqueous solution gives a yield of more than 20% of polybenzylbenzenes and of only from 0 to 47% of diphenylmethane, even at temperatures as low as 50° C. The specific effect of the catalyst is singled out in this publication as being the decisive unpredictable factor.

Japanese Published Application No. 40,754/1973 discloses that o-xylyl halides can be condensed with aromatic compounds in the presence of sulfuric acid provided more than 7 moles of aromatic compounds are employed per mole of the halide. From the description given it was natural to assume that the condensation of the halide with itself, and sulfonation reactions, were repressed substantially by the high dilution of the starting mixture, the aromatic compound acting as a diluent. The Japanese publication states that during the reaction the 2-phase reaction mixture is constantly in the form of two separate layers. The sulfuric acid is throughout used in an amount of from 0.5 to 2 moles per mole of o-xylyl chloride. The reaction temperature is from 45° to 78° C. The description and in particular the example show that the volume ratio of organic layer is aqueous layer of the 2-phase reaction mixture is very high, and far above 10 : 1. The use of stirring means is mentioned in the description, but no details regarding suitable apparatus and conditions are provided.

It is an object of the present invention to provide a new process whereby o-benzyltoluenes can be manufactured more simply and more economically, in good yield and high purity.

We have found that o-benzyltoluenes of the formula

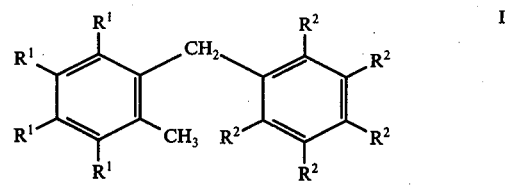

in which the individual $R^1$s are identical or different and each is hydrogen or halogen and the individual $R^2$s are identical or different and each is hydrogen, halogen, an aliphatic radical or an aromatic radical, are obtained advantageously by reaction of o-xylyl halides with aromatic compounds by a method wherein o-xylyl halides of the formula

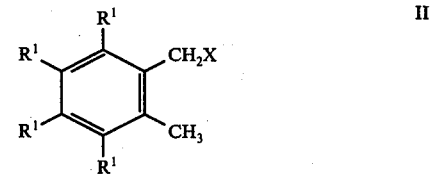

where $R^1$ has the above meanings and X is halogen, are reacted with benzenes of the formula

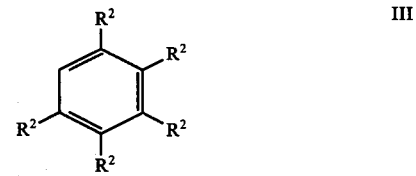

where $R^2$ has the above meanings, in the presence of sulfuric acid or, in place of sulfuric acid, in the presence of phosphoric acid and of organic sulfonic acids, zinc compounds and/or tin compounds or, in addition to sulfuric acid, in the presence of phosphoric acid, organic sulfonic acids, boron compounds, zinc compounds and/or tin compounds, using a ratio of less than 7 moles of starting material III per mole of starting material II, or, additionally to sulfuric acid, in the presence of phosphoric acid, organic sulfonic acids, boron compounds, zinc compounds and/or tin compounds or, instead of sulfuric acid, in the presence of phosphoric acid and of organic sulfonic acids, zinc compounds and/or tin compounds, using a ratio of at least 7 moles of starting material III per mole of starting material II.

Further, we have found that the above process can be carried out advantageously by effecting the reacton with from 3 to 15 moles of sulfuric acid per mole of starting material III.

Further, we have found that the above process can be carried out advantageously by effecting the reaction with a volume ratio of from 0.5 to 2 parts by volume of organic phase per part by volume of aqueous phase in the reaction mixture.

Further, we have found that the above process can be carried out advvantageously by effecting the reaction in a finely dispersed mixture of the organic phase in the aqueous phase, the droplets of the organic phase being at most 1,000 nanometers in size.

Further, we have found that the process can be carried out advantageously by effecting the reaction in the presence of sulfuric acid with a ratio of less than 7 moles of starting material III per mole of starting material II.

Further, we have found that the process can be carried out advantageously by effecting the reaction with a ratio of less than 7 moles of starting material III per mole of starting material II in the presence of phosphoric acid and of organic sulfonic acids, zinc compounds and/or tin compounds, in place of sulfuric acid.

Further, we have found that the process can be carried out advantageously by effecting the reaction with a ratio of less than 7 moles of starting material III per mole of starting material II in the presence of phosphoric acid, organic sulfonic acids, boron compounds, zinc compounds and/or tin compounds, in addition to sulfuric acid.

Further, we have found that the process can be carried out advantageously by effecting the reaction with a ratio of at least 7 moles of starting material III per mole of starting material II in the presence of phosphoric acid, organic sulfonic acids, boron compounds, zinc compounds and/or tin compounds additionally to sulfuric acid, or in the presence of phosphoric acid and of organic sulfonic acids, zinc compounds and/or tin compounds in place of sulfuric acid.

Where o-xylyl chloride and benzene are used, the reaction can be represented by the following equation:

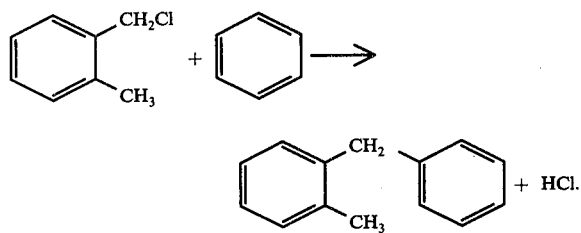

Compared to conventional processes, the process according to the invention gives o-benzyltoluenes more simply and more economically, and in good yield and high purity. Compared to the processes first mentioned, which are aralkyl chlorides, the yield and purity of the end product is better and the isolation of the end product from the reaction mixture is substantially simpler and more reliable. Compared to the state of the art, the process according to the invention is simpler, involves less problems and is therefore particularly suitable for industrial use. The starting materials are easily obtainable and their manufacture does not entail involved and/or multi-stage syntheses.

Compared to the process described in the Japanese publication, the process according to the invention can be carried out with smaller amounts of starting material III and is therefore simpler and more economical. Since the starting materials III are in most cases flammable solvents, or are toxic or volatile substances which pollute the atmosphere, the process according to the invention is safer in operation, improves and simplifies monitoring and control of the reaction even on an industrial scale, facilities safeguarding the health of operatives, reduces the problems of detoxication of the off-gases, purification of effluents and avoidance of atmospheric pollution, and thus represents an advance from an environmental and ecological point of view.

Compared to the process described in the Japanese publication, the process according to the invention is safer in industrial operation, in particular in continuous operation, even if higher amounts of starting material III are used. In the case of the conventional process, the yield and reaction rate greatly depend on the concentration of sulfuric acid. However, it is difficult to maintain a constant and defined acid concentration in an industrial process which uses the same catalyst for prolonged periods. The process according to the invention has the advantage that the acid concentration is allowed to vary within a substantial range.

All these advantages are surprising in the light of the state of the art, because it would have been expected, from a knowledge of Friedel-Crafts syntheses and from the teaching of the above Japanese patent application, that alkylated aromatics would be aralkylated much more easily than, e.g., benzene, and that accordingly o-xylyl halides would preferentially react with themselves and only to a lesser degree with benzene. Since, contrary to this teaching, the reaction is carried out with substantially smaller amounts of starting material III and preferably with a substantially lower volume ratio of organic layer to aqueous layer in the reaction mixture, and also with higher amounts of sulfuric acid, based on starting material II, and at higher temperatures, it was to be feared that substantial amounts of dibenzyl compounds and of sulfonated end products and by-products would be formed. In contrast to the conventional processes, particularly thorough mixing of the reaction mixture is preferred in the process according to the invention. Hence, compared to the state of the art, it is not only the ratio of the starting materials but also the preferred features of the volume ratio of the phases, the amount of sulfuric acid used and the rate of stirring which are surprising. The formation of sulfonation products would also have been expected from the state of the art.

Some of the embodiments of the process are carried out with a ratio of less than 7 moles of starting material III per mole of starting material II, and some with a ratio of at least 7 moles of starting material III per mole of starting material II. In the case of the lower molar ratio of the starting material, the starting material III is reacted with stoichiometric amounts of the starting material II, or using an excess of less than 6 moles of starting material III, preferably using a ratio of from 2 to 6 moles, in particular of from 4 to 6 moles, of starting material III per mole of starting material II. In the case of the higher molar ratio, the starting material III is reacted with the starting material II in an amount of 7 or more moles of starting material III per mole of starting material II, preferably using a ratio of from 9 to 15 moles, in particular of from 10 to 12 moles, of starting material III per mole of starting material II.

Preferred starting materials II and III, and, accordingly, preferred end products I are those wherein the individual radicals $R^1$ and $R^2$ are identical or different and each is hydrogen or chlorine or bromine, and the radicals $R^2$ can also each be alkyl of 1 to 6 carbon atoms or phenyl, and X is bromine or preferably chlorine. The above radicals can in addition be substituted by groups and/or atoms which are inert under the reaction conditions, e.g. by alkyl of 1 to 4 carbon atoms.

Examples of suitable starting materials II are o-xylyl chloride, 3-chloro-2-chloromethyl-toluene, 4-chloro-2-chloromethyl-toluene, 5-chloro-2-chloromethyl-toluene, 6-chloro-2-chloromethyl-toluene, 6-bromo-2-chloromethyl-toluene, 4-bromo-2-chloromethyl-toluene, 3-bromo-2-chloromethyl-toluene, 5-bromo-2-chloromethyl-toluene and analogous bromomethyl compounds.

Examples of suitable starting material III are benzene, toluene, o-xylene, m-xylene, p-xylene, diphenyl, 1,4-diphenylbenzene, 1,2,3-trimethylbenzene, 1,2,4-trimethylbenzene, 1,3,5-trimethylbenzene, 1,2,3,4-tetramethylbenzene, 1,2,3,5-tetramethylbenzene, 1,2,4,5-tetramethylbenzene, pentamethylbenzene, chlorobenzene, bromobenzene, o-chlorotoluene, m-chlorotoluene, p-chlorotoluene, p-bromo-ethyl-benzene, tert.-butylbenzene and 4,4'-dichlorodiphenyl.

In general, the reaction is carried out at from 40° to 160° C, preferably from 60 to 130° C, especially from 75 to 90° C, under atmospheric or superatmospheric pressure, batchwise or continuously. It is advantageous to use solvents which are inert under the reaction conditions, e.g. water, aromatic hydrocarbons, such as nitrobenzene and trichlorobenzene, chlorohydrocarbons, such as methylene chloride, ethylene chloride, carbon tetrachloride and chloroform, carbon disulfide, aliphatic hydrocarbons such as ligroin and petroleum ether, or appropriate mixtures. From 10 to 100% by weight of solvent, based on starting material II, can be used. The starting material III can itself also act as the solvent.

In a preferred embodiment, sulfuric acid is used by itself; as a rule, it is concentrated sulfuric acid of from 50 to 100% strength by weight, preferably of from 70 to 90% strength by weight and suitably of from 75 to 85% strength by weight and, where sulfuric acid alone is used and the molar ratio of the starting materials is low, in particular of from 78 to 82% strength by weight and in an amount of at least 3 moles, preferably of from 3 to 15 moles, and especially of from 3 to 6 moles, of sulfuric acid (expressed as 100% strength material) per mole of starting material II.

In a further preferred embodiment, phosphoric acid and adjuvants, preferably one adjuvant, are used in place of sulfuric acid. The adjuvants are organic sulfonic acids, zinc compounds and/or tin compounds. Phosphoric acid is preferably used in an amount of from 1 to 20 moles, preferably of from 3 to 10 moles (expressed as 100% strength material), based on starting material II. The phosphoric acid is taken, for calculation purposes, as 100% strength by weight orthophosphoric acid, regardless of its true structure, though it is possible to use, e.g., metaphosphoric acid, pyrophosphoric acid or, in particular, orthophosphoric acid, suitably in the form of an aqueous solution containing from 50 to 90 per cent by weight of phosphorous pentoxide, preferably from 60 to 80 per cent by weight of phosphorous pentoxide. The phosphoric acid can also be a polyphhosphoric acid, for example containing from 72 to 88 per cent by weight of $P_2O_5$; it is also possible to add phosphorous pentoxide, preferably in amounts corresponding to the polyphosphoric acids, in addition to phosphoric acid of the above concentrations.

The sulfonic acids used can be aliphatic or aromatic sulfonic acids. In general, from 0.2 to 1.0 mole, preferably from 0.4 to 0.7 mole, of sulfonic acid, based on starting material II, is used, both in the case of only one adjuvant and in the case of mixtures of several adjuvants. Sulfonic acids which can be used advantageously are monoalkanesulfonic acids of 1 to 6 carbon atoms, especially methanesulfonic acid, ethanesulfonic acid, propane-1-sulfonic acid, n-butane-1-sulfonic acid, n-pentane-1-sulfonic acid, n-hexane-1-sulfonic acid; alkanedisulfonic acids of 1 to 6 carbon atoms, especially methanedisulfonic acid and ethane-1,2-disulfonic acid; halogenoalkanesulfonic acids and hydroxyalkanesulfonic acids of 1 to 6 carbon atoms, especially 2-chloroethane-1-sulfonic acid, 2-hydroxy-1-ethanesulfonic acid, 3-hydroxypropane-1sulfonic acid, 3-hydroxybutane-1-sulfonic acid, 4-hydroxybutane-1-sulfonic acid, 1-chlorobutane-3sulfonic acid and 1-chlorobutane-4-sulfonic acid; perfluorinated alkanesulfonic acids of 1 to 6 carbon atoms, especially perfluoromethanesulfonic acid, perfluoroethanesulfonic acid, perfluoropropane-1-sulfonic acid, perfluorobutane-1sulfonic acid, perfluoropentane-1-sulfonic acid and perfluorohexane-1-sulfonic acid; benzenesulfonic acids, especially benzenemonosulfonic acid, benzene-1,2-disulfonic acid, benzene-1,3-disulfonic acid and benzene-1,4-disulfonic acid; 2-methylbenzenesulfonic acid, 3-methylbenzenesulfonic acid, 4-methylbenzenesulfonic acid, 2,4-dimethylbenzenesulfonic acid, 2,5-dimethylbenzenesulfonic acid, 2,4,5-trimethylbenzenesulfonic acid, 4-isopropylbenzenesulfonic acid, 4-n-octylbenzenesulfonic acid and 4-dodecylbenzenesulfonic acid; partially hydrogenated aromatic sulfonic acids, such as indan-5-sulfonic acid and tetralin-2-sulfonic acid; carboxybenzenesulfonic acids, halogenobenzenesulfonic acids and hydroxybenzenesulfonic acids, especially 2-carboxybenzenesulfonic acid, 3-carboxybenzenesulfonic acid, 4-carboxybenzenesulfonic acid, 3,5-dicarboxybenzenesulfonic acid, 3,4-dicarboxybenzenesulfonic acid, 2-chloro-5-carboxybenzenesulfonic acid, 3-chloro-4-carboxy-benzenesulfonic acid, 4-chlorobenzenesulfonic acid, 3-chlorobenzenesulfonic acid, 2-chlorobenzenesulfonic acid, 2,5-dichlorobenzenesulfonic acid, 3,4-dichlorobenzenesulfonic acid, 2,4,5-trichlorobenzenesulfonic acid, 2-hydroxybenzenesulfonic acid, 3-hydroxybenzenesulfonic acid, 4-hydroxy-benzenesulfonic acid, 3-chloro-4-methylbenzenesulfonic acid, 5-chloro-2-methylbenzenesulfonic acid, 4-chloro-3-methylbenzenesulfonic acid, 3-chloro-4-hydroxybenzenesulfonic acid and 5-chloro-2-hydroxybenzenesulfonic acid; polynuclear aromatic sulfonic acids, especially benzophenone-4,4'-disulfonic acid, diphenylmethane-4,4'-disulfonic acid, diphenylsulfone-3,3'-disulfonic acid, napthalene-1-sulfonic acid, naphthalene-2-sulfonic acid, naphthalene-1,5-disulfonic acid, napthalene-1,6-disulfonic acid, naphthalene-2,6-disulfonic acid, naphthalene-2,7-disulfonic acid, naphthalene-1,3,6-trisulfonic acid, diphenylether-4,4'-disulfonic acid, acenaphthene-3-sulfonic acid and acenaphthene-5-sulfonic acid.

As a rule, the zinc compounds or tin compounds are employed in amounts of from 0.5 to 2 moles, preferably of from 0.8 to 1.5 moles of an individual adjuvant or a mixture of several adjuvants, per mole of starting material II. Suitable zinc compounds and tin compounds are halides, especially zinc chloride, zince fluoride, zinc bromide, tin-II chloride, tin-IV chloride, tin-IV fluoride and tin-II fluoride, alkali metal tetrachlorozincates and alkaline earth metal tetrachlorozincates, such as disodium tetrachlorozincates, basic zinc chlorides, such as zinc hydroxy-chloride, halogenostannates, such as ammonium hexafluostannate and ammonium hexachlorostannate, tin-IV bromide, zinc oxalate, zinc carbonate, zinc sulfate and tin-II sulfate, Lewis acids and complex compounds, such as zinc acetate or tin acetate and their glycerol complexes.

Toluenesulfonic acid, trifluoromethanesulfonic acid, zinc chloride and tin-IV chloride are particularly preferred adjuvants.

In a further preferred embodiment of the reaction, sulfuric acid and one or more adjuvants can be used. In that case, the adjuvants are phosphoric acid, organic sulfonic acids, boron compounds, zinc compounds and/or tin compounds. Preferred embodiments are the use of sulfuric acid and one adjuvant, or of sulfuric acid and phosphoric acid together with a sulfonic acid, or of sulfuric acid and phosphoric acid together with a boron compound, or of sulfuric acid and phosphoric acid together with one of the metal compounds. In advantageous and preferred embodiments, the phosphoric acid, sulfonic acids, zinc compounds and tin compounds are those mentioned earlier and are used in the amounts mentioned earlier. Suitable mixtures of phosphoric acid and sulfuric acid, with or without water, and of phosphorus pentoxide and dilute sulfuric acid can also be used. In conjunction with sulfuric acid, optionally together with adjuvants, the amount of sulfonic acid used is in general from 0.1 to 1.0 mole, preferably from 0.3 to 0.7 mole, based on starting material II, regardless of whether one adjuvant or mixtures of several adjuvants are used.

The boron compounds are as a rule employed in amounts of from 0.5 to 2 moles, preferably from 0.8 to 1.5 moles, per mole of starting material II, and are employed either individually or as a mixture of several adjuvants. Suitable adjuvants are one or more optionally chosen, organic or preferably inorganic, liquid or preferably solid, compounds of trivalent boron. Examples are boron halides and their coordination compounds, such as boron trichloride, fluoboric acid, sodium fluoborate and potassium fluoborate, boron sulfide, boron nitride and boron-phosphorus oxide; coordination compounds of trivalent boron with organic compounds, especially with dihydroxy compounds, such as dipyrocatechol borates, e.g. sodium dipyrocatechol borate, monoglycerol and diglycerol borates, phenylglycol borates and pentane-2,4-diol borates, boron-acyl compounds such as boron triphenyl, metal borides such as magnesium boride, boric acid esters such as triethyl borate, methyl dichloroborate and dimethyl monochloroborate, boric acids, such as metaboric acid, tetraboric acid and especially orthoboric acid, the corresponding borates, especially alkali metal borates, such as borax, lithium borate, potassium pentaborate, sodium metaborate, ammonium borate, calcium borate, zinc borate, barium borate and magnesium borate, and boron trioxide. The preferred adjuvant is boron trifluoride and/or the complex compound of a boron trifluoride. Examples of complex compounds of boron trifluoride which can be used are the complexes with the following: phosphoric acid, hydrogen fluoride, nitrogen compounds such as ammonia, amines or nitric oxide, ethanol, water (e.g. in the form of the dihydrate of boron trifluoride) and ethers, e.g. dimethyl ether. It is also possible to use materials which form such complex compounds in situ, e.g. alkali metal phosphates, alkali metal fluorides and boron trifluoride in an acid reaction mixture, or which contain such complex compounds, for example oxo-fluoboric acids, alkali metal fluoborates, zinc fluoborate and tin fluoborate. Examples of boron trichloride complexes which can be used are those with phosphorus trichloride, phosphorus oxychloride and nitrosyl chloride. In the complex compound, the molar ratio of boron trifluoride to the other constituent of the complex is in general 1:1 or, in the case of water, 1:2.

Particularly preferred adjuvants in this preferred embodiment are phosphoric acid, toluenesulfonic acid, trifluoromethanesulfonic acid, boron fluoride, zinc chloride, tin-IV chloride and boron fluoride dihydrate.

When the reaction is carried out using a ratio of at least 7 moles of starting material III to 1 mole of starting material II, sulfuric acid is used together with phosphoric acid, or either of two acids is used together with one or more of the above adjuvants. Preferred embodiments are the combination of the acids with or without a further adjuvant, i.e. a sulfonic acid, boron compound, zinc compound or tin compound, the combination of sulfuric acid and an adjuvant and the combination of phosphoric acid and an adjuvant. With regard to phosphoric acid and the adjuvants, it is advantageous to use the compounds, amounts and preferred characteristics mentioned earlier.

The total volume of the starting materials II and III, of the adjuvants, of the solvent, of the phosphoric acid and of the sulfuric acid are preferably so chosen that during the entire reaction a volume ratio of from 0.5 to 2, especially of from 0.9 to 1.1, parts by volume of organic phase per part by volume of aqueous phase is maintained in the 2-phase starting mixture or reaction mixture.

The reaction can be carried out as follows: a mixture of starting materials II and III, of the acid or acids and, where relevant, of the adjuvants and of the solvent, is kept at the reaction temperature for from 2 to 15 hours, whilst undergoing thorough mixing. The mixture is then cooled and the end product is isolated by conventional methods, e.g. by separating off, and distilling, the organic phase.

In a preferred embodiment of the process, the reaction mixture is subjected to thorough mixing throughout the reaction, preferably by stirring it at not less than 700, especially at from 850 to 2,000, revolutions per minute. If mixing devices without stirrers are used, the preferred devices subject the mixture to a shear energy corresponding to the above speed of stirring. This gives a finely dispersed mixture, preferably an emulsion. If appropriate, emulsifiers can be added to form emulsions. Finely disperse mixtures of the organic phase in the aqueous phase, preferably emulsions, in which the size of the droplets is at most 1,000 advantageously from 1 to 600, preferably from 5 to 400, and especially from 5 to 300, nanometers, are used preferentially. Provided the above mixing conditions are observed, a wide range of conventional stirring devices can be used, namely injectors, ball jets, vortex jets, turbine stirrers, mixing nozzles, Lechler mixing nozzles, paddle stirrers, anchor stirrers, bar-type stirrers, propeller stirrers, Cramer stirrers, vibro-mixers, finger-type stirrers, crossbeam stirrers, gyratory stirrers, grid stirrers, flat stirrers, spiral turbines, scoop stirrers, planetary stirrers, centrifugal gyratory stirrers, rotating atomizers, ejectors, triangular stirrers, hollow stirrers, tubular stirrers and impeller stirrers; impeller stirrers and mixing nozzles are preferred. It is also possible to use equipment which permits thorough mixing, such as stirred kettles, stirred kettle cascades, flow tubes, air-lift type stirring units, homogenizing equipment, gyratory mixers, turbomixers, emulsifying centrifuges, ultrasonic tubes, flow mixers, rotating drums, chamber reactors, circulatory reactors, loop reactors, cellular reactors, screw reactors, bubble columns, jet scrubbers, liquid ring pumps, ejector-type tubular reactors and thin film reactors; stirred kettle cascades, loop reactors and ejector-type reactors preferred.

The side-chain halogenation of halogenoxylenes to form the starting materials II, for example the side-chain chlorination of 3-chloro-o-xylene or 4-chloro-o-xylene, produces two isomeric halogeno-o-xylyl halides, namely 3-chloro-2-chloromethyl-toluene and 6-chloro-2-chloromethyl-toluene or 4-chloro-2-chloromethyl-toluene and 5-chloro-2-chloromethyl-toluene in the case of the examples chosen, and these products, on reaction with benzenes III, each give two corresponding isomeric benzylchlorotoluenes. On oxidation of the mixtures to the corresponding o-benzolybenzoic acids and subsequent cyclization, uniformly substituted anthraquinones are obtained, namely 1-chloro-anthraquinone and 2-chloro-anthraquinone in the case of the examples chosen. The end products I can be isolated from the mixtures mentioned by suitable operations, e.g. fractional distillation or fractional crystallization. In general, however, the reaction is carried out with a mixture of starting materials II and the resulting mixture of end products I is used as such for the next stage. For the same reason, it is in most cases convenient to subject mixtures of 3-chloro-o-xylene and 4-chloro-o-xylene, such as are obtained, e.g., on chlorination of o-xylene, to side-chain chlorination, then to react the resulting mixture of 4 isomeric starting materials II in accordance with the process of the invention, and only to separate the resulting mixture of the 4 end products I after cyclization to the chloroanthracenes. The process according to the invention is therefore important not only for the manufacture of individual end products, but also for the manufacture of these mixtures, which are important starting materials for the synthesis of dyes, particularly in industry.

The o-benzyltoluenes I manufactured by the process according to the invention are valuable starting materials for the manufacture of anthracene and anthraquinone and their derivatives. Thus anthracene derivatives are formed on passing the vapors of o-benzyltoluenes over lead oxide. The oxidation of o-benzyltoluenes with nitric acid gives o-benzoylbenzoic acid and its derivatives. With regard to the use of the products, reference may be made to the publications mentioned earlier and to Ullmanns Encyklopadie der technischen Chemie, volume 3, 600 et seq.

Advantageous end products I, in the above context, are o-benzyltoluenes of the formula

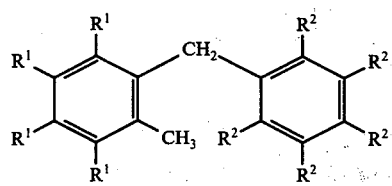

wherein the individual radicals $R^1$ are identical or different and each is hydrogen or halogen and the individual radicals $R^2$ are identical or different and each is an aromatic radical, and in addition the individual radicals $R^2$ can also each be hydrogen or an aliphatic radical if at least one radical $R^1$ is halogen, or all radicals $R^1$ can be hydrogen if at least one radical $R^2$ is an aromatic radical and the remaining radicals $R^2$ are each hydrogen, halogen and/or an aliphatic radical or if, in a given molecule, at least one radical $R^2$ is halogen, at least one radical $R^2$ is an aliphatic radical and the remaining radicals $R^2$ are each hydrogen, halogen and/or an aliphatic radical.

Preferred end products I are o-benzyltoluenes of the formula

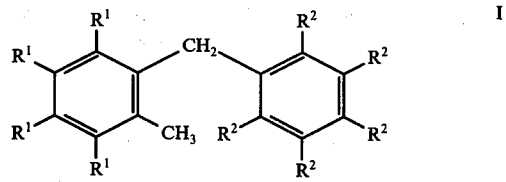

wherein the individual radicals $R^1$ are identical or different and each is hydrogen or chlorine or bromine, and the individual radicals $R^2$ are identical or different and each is phenyl, and furthermore the individual radicals $R^2$ can each be hydrogen or alkyl of 1 to 6 carbon atoms if at least one radical $R^1$ is chlorine or bromine, or all radicals $R^1$ can be hydrogen if at least one radical $R^2$ is phenyl and the remaining radicals $R^2$ are each hydrogen, chlorine, bromine and/or alkyl of 1 to 6 carbon atoms, or if, in a given molecule, at least one radical $R^2$ is chlorine or bromine, at least one radical $R^2$ is alkyl of 1 to 6 carbon atoms and the remaining radicals $R^2$ are each hydrogen, chlorine, bromine, and/or alkyl of 1 to 6 carbon atoms.

Particularly preferred end products I are o-benzyltoluenes of the formula

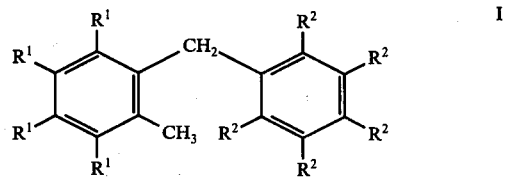

wherein the individual radicals $R^1$ are identical or different and each is hydrogen or chlorine, but at least one radical $R^1$ is chlorine, and the individual radicals $R^2$ are each hydrogen. Further particularly preferred end products I are o-benzyltoluenes of the formula

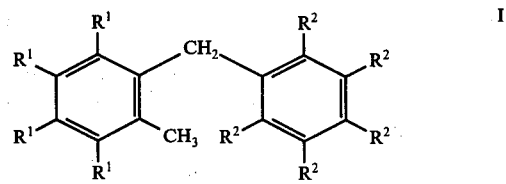

wherein the individual radicals $R^1$ are each hydrogen and the individual radicals $R^2$ are identical or different and at least one radical $R^2$ is phenyl or one radical $R^2$ is chlorine and a further radical $R^2$ is methyl, and the remaining radicals $R^2$ are each hydrogen.

Examples of particularly preferred end products I are 2-benzyl-toluene, 2-benzyl-3-chlorotoluene, 2-benzyl-6-chlorotoluene, 2-benzyl-4-chlorotoluene, 2-benzyl-5- chlorotoluene, 2,2'-dimethyl-5-chlorodiphenylmethane and 2-methyl-4'-phenyldiphenylmethane.

The parts in the Examples are parts by weight.

EXAMPLE 1

A solution of 70 parts of o-xylyl chloride in 230 parts of benzene is added to 350 parts of 75 per cent strength by weight sulfuric acid at 80° C in a stirred vessel, the mixture being stirred with an impeller stirrer at 900 revolutions per minute. After a further 5 hours at 80° C, during which the batch is mixed thoroughly, the organic phase is separated off and 73 parts (= 81.1% of theory) of o-benzyltoluene boiling at from 97° to 100° C at 0.2 mm Hg, and of $n_D^{25} = 1.5749$, are isolated by distillation.

EXAMPLE 2

The procedure of Example 1 is followed, but instead of the 75 per cent strength by weight sulfuric acid, the same quantity of 80 per cent strength by weight sulfuric acid is used. Yield: 80.2 parts (= 89% of theory) of o-benzyltoluene boiling at from 97° to 100° C at 0.2 mm Hg.

EXAMPLE 3

The procedure of Example 1 is followed, but instead of 75 per cent strength by weight sulfuric acid, 85 per cent strength by weight sulfuric acid is used. The reaction temperature is from 68° to 70° C. Yield: 78 parts (= 86.6% of theory) of o-benzyltoluene boiling at from 97° to 100° C.

EXAMPLE 4

3,660 parts of 80 per cent strength by weight sulfuric acid are circulated in a loop reactor by means of a centrifugal pump. A solution of 1,120 parts of o-xylyl chloride and 3,120 parts of benzene is added at from 75° to 77° C in the course of 3½ hours, resulting in the formation of an emulsion. A part of the emulsion is allowed to run continuously from an overflow into a settling vessel. The organic phase is separated off and distilled and the inorganic phase is returned to the circulation system. 1,334 parts (91.9% of theory) of o-benzyltoluene boiling at from 100° to 104° C at 0.3 mm Hg are isolated from the organic phase by distillation.

EXAMPLE 5

850 parts of 80 per cent strength by weight sulfuric acid are introduced into a vessel equipped with an impeller stirrer. A solution of 70 parts of o-xylyl chloride and 156 parts of benzene in 200 parts of ligroin are run in at from 75° to 80° C, whilst stirring thoroughly. After a further 5 hours at 80° C, the organic phase is separated off and 75 parts (83% of theory) of o-benzyltoluene boiling at from 97 to 100° C at 0.2 mm Hg are isolated by distillation.

EXAMPLE 6

A solution of 95 parts of 2-chloromethyl-6-chlorotoluene and 80 parts of 2-chloromethyl-3-chlorotoluene in 470 parts of benzene is added to 300 parts of 80 per cent strength by weight sulfuric acid at from 75° to 80° C, whilst stirring thoroughly. After a further 5 hours at 80° C, the organic phase is separated off and 170.9 parts (79% of theory) of a mixture of 2-benzyl-6-chlorotoluene and 2-benzyl-3-chlorotoluene in the weight ratio corresponding to the starting materials is isolated by fractional distillation; the mixture boils at from 175° to 177° C at 17 mm Hg.

EXAMPLE 7

The procedure of Example 2 is followed, except that 250 parts of toluene are used instead of benzene. Yield: 82 parts (83.7% of theory) of 2-(methylbenzyl)-toluene boiling at from 98° to 101° C at 0.1 mm Hg.

EXAMPLE 8

A solution of 70 parts of o-xylyl chloride and 160 parts of benzene is added to a mixture of 170 parts of 85 per cent strength by weight phosphoric acid and 30 parts of trifluoromethanesulfonic acid at from 75° to 78° C, whilst stirring vigorously. After a further 6 hours, the organic phase is separated off and 79 parts (87.7% of theory) of o-benzyltoluene boiling at 98° C at 0.2 mm Hg are isolated by distillation.

EXAMPLE 9

A solution of 70 parts of o-xylyl chloride and 200 parts of benzene is added to a mixture of 170 parts of 85 per cent strength by weight phosphoric acid, 22 parts of water and 75 parts of zinc chloride at 75° to 80° C, whilst stirring thoroughly. After a further 5 hours, the organic phase is separated off and 78 parts (86.6% of theory) of o-benzyltoluene boiling at 98° C at 0.2 mm Hg are isolated by fractional distillation.

EXAMPLE 10

The procedure of Example 8 is followed, except that the reaction mixture is worked up after only 2 hours. Fractional distillation gives 20 parts of unconverted o-xylyl chloride, which can be reused as starting material, and 58.5 parts (91% of theory, based on o-xylyl chloride converted) of o-benzyltoluene boiling at 98° C at 0.2 mm Hg.

EXAMPLE 11

A solution of 95 parts of 2-chloromethyl-6-chlorotoluene and 80 parts of 2-chloromethyl-3-chlorotoluene and 80 parts of xylene is added to a mixture of 170 parts of 85 per cent strength by weight phosphoric acid, 20 parts of trifluoromethanesulfonic acid and 20 parts of p-toluenesulfonic acid at from 80° to 85° C. After a further 5 hours, the organic phase is separated off and 220 parts (90% of theory) of a 1:1 mixture of 2-chloro- and 5-chloro-6,2',5'-trimethyl-diphenylmethane boiling at from 125° to 127° C at 0.2 mm Hg are isolated by fractional distillation.

EXAMPLE 12

A solution of 140 parts of o-xylyl chloride and 500 parts of benzene is added to a mixture of 162 parts of boron fluoride dihydrate and 16 parts of sulfuric acid monohydrate at from 75° to 78° C, whilst stirring vigorously. After a further 6 hours, the organic phase is separated off and 162 parts (90% of theory) of o-benzyltoluene boiling at 98° C at 0.2 mm Hg are isolated by distillation.

EXAMPLE 13

A solution of 70 parts of xylyl chloride in 240 parts of benzene is added to a mixture of 60 parts of boron fluoride dihydrate and 250 parts of 75 per cent strength by weight sulfuric acid at from 75° to 78° C, whilst stirring vigorously. After 6 hours, the organic phase is separated off and 82 parts (91.1% of theory) of o-benzyl-toluene boiling at 98° C at 0.2 mm Hg are isolated by distillation.

EXAMPLE 14

A solution of 70 parts of o-xylyl chloride and 240 parts of benzene is added to a mixture of 250 parts of 75 percent strength by weight sulfuric acid and 30 parts of zinc chloride at from 75° to 80° C, whilst stirring thoroughly. After a further 6 hours, the organic phase is separated off and 80 parts (88.9% of theory) of o-benzyltoluene boiling at 98° C at 0.2 mm Hg are isolated by distillation.

EXAMPLE 15

A solution of 70 parts of o-xylyl chloride and 200 parts of benzene is added in the course of 2 hours, whilst stirring thoroughly, to a mixture of 250 parts of 70 per cent strength by weight sulfuric acid and 72 parts of phosphorus pentoxide at from 75° to 77° C. After a further 4 hours at from 75° to 77° C, the organic phase is separated off and 80.9 parts (89.8% of theory) of o-benzyltoluene boiling at 98° C at 0.2 mm Hg are isolated by fractional distillation.

EXAMPLE 16

A solution of 70 parts of o-xylyl chloride and 240 parts of benzene is added to a mixture of 135 parts of 80 per cent strength by weight sulfuric acid and 135 parts of 85 per cent strength by weight phosphoric acid at from 75° to 77° C, whilst stirring thoroughly. After a further 5 hours at from 75° to 77° C, 200 parts of water are added, the organic phase is separated off and 80 parts (88.9% of theory) of o-benzyltoluene boiling at 98°C at 0.2 mm Hg are isolated by distillation.

EXAMPLE 17

A mixture of 3,200 parts of concentrated sulfuric acid (98% strength by weight), 400 parts of water and 1,800 parts of 85 per cent strength by weight phosphoric acid is circulated in a reactor by pumping with a centrifugal pump. A solution of 1,680 parts of o-xylyl chloride and 4,680 parts of benzene is added in the course of 3½ hours at from 75° to 77° C; an emulsion forms. A part of the emulsion is fed continuously from an overflow into a receiver. The inorganic phase is returned to the circulation system and the organic phase is distilled. 2,023 parts (93.6% of theory) of o-benzyltoluene boiling at 98° C at 0.2 mm Hg are isolated.

EXAMPLE 18

A mixture of 71 parts of o-xylyl chloride and 300 parts of o-xylene is added in the course of one hour, whilst stirring thoroughly, to a mixture of 228 parts of 85 per cent strength by weight phosphoric acid, 30 parts of water, 240 parts of concentrated sulfuric acid and 10 parts of naphthalene-2,7-disulfonic acid at from 75° to 80° C. After a further 5 hours at from 75° to 80° C, the organic phase is separated off and 96.6 parts (92% of theory) of 2,3',4'-trimethyldiphenylmethane boiling at from 110° to 112° C at 0.05 mm Hg are isolated by fractional distillation.

EXAMPLE 19

A solution of 70 parts of o-xylyl chloride and 390 parts of benzene is added to a mixture of 135 parts of 85% strength by weight phosphoric acid, 270 parts of 85% strength by weight sulfuric acid and 10 parts of p-toluenesulfonic acid at from 75° to 80° C, whilst stirring thoroughly. After a further 4 hours at from 75° to 80° C the organic phase is separated off and 81 parts (89% of theory) of o-benzyltoluene ($n_D^{25}$: 1.5739) are isolated by distillation at from 98° to 100° C at 0.2 mm Hg.

EXAMPLE 20

A solution of 44 parts of 4-chloro-2-chloromethyltoluene and 44 parts of 5-chloro-2-chloromethyltoluene in 390 parts of benzene is added in the course of 2 hours, at from 75° to 80° C, to a mixture of 135 parts of 85% strength by weight phosphoric acid, 240 parts of 98% strength by weight sulfuric acid and 30 parts of ice, whilst stirring thoroughly. After 8 hours, the organic phase is separated off and 30 parts of unchanged toluene starting material are isolated by distillation, followed, at from 118° to 120° C at 0.1 mm Hg, by 64 parts (89.7% of theory, based on converted starting material) of 4- and 5-chloro-2-benzyltoluene in the ratio 1:1.

EXAMPLE 21

A solution of 70 parts of o-xylyl chloride in 530 parts of p-xylene is added, at from 75° to 80° C, to a mixture of 120 parts of phosphoric acid, 212 parts of 85% strength by weight sulfuric acid, 42 parts of ice and 10 parts of zinc chloride, whilst stirring thoroughly. After a further 5 hours at from 75° to 80° C, the organic phase is separated off and 100 parts (95.2% of theory) of 2,2',5'-trimethyldiphenylmethane ($n_D^{25}$: 1.5687) are isolated by distillation at 130° to 132° C at 0.3 mm Hg.

EXAMPLE 22

A solution of 70 parts of o-xylyl chloride and 420 parts of toluene is added to a mixture of 350 parts of phosphoric acid (85% strength by weight) and 100 parts of zinc chloride at from 85° to 90° C, whilst stirring thoroughly. After a further 8 hours, the organic phase is separated off and 85 parts (86.7% of theory) of 2,4'-dimethylmethane ($n_D^{25}$: 1.5674) are isolated by distillation at from 115° to 116° C at 0.2 mm Hg.

EXAMPLE 23

470 parts of benzene are emulsified in a mixture of 200 parts of boron fluoride-phosphoric acid (containing 90 parts of boron fluoride in 110 parts of phosphoric acid) and 200 parts of sulfuric acid (85% strength by weight) by stirring thoroughly. A solution of 140 parts of o-xylyl chloride in 470 parts of benzene is added at from 75° to 80° C in the course of 2 hours. The reaction mixture is stirred for a further 5 hours at from 75° to 80° C and the organic phase is then separated off. 167 parts (91.8% of theory) of o-benzyltoluene ($n_D^{25}$: 1.5739) are isolated by fractional distillation at from 98° to 100° C at 0.2 mm Hg.

We claim:
1. In a process for the manufacture of an o-benzyltoluene of the formula

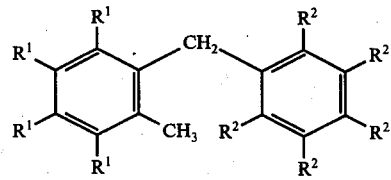

in which each $R^1$ is hydrogen or halogen and each $R^2$ is hydrogen, halogen, an aliphatic radical or an aromatic radical, by the reaction of an o-xylyl halide with an aromatic compound, the improvement which comprises reacting an o-xylyl halide of the formula

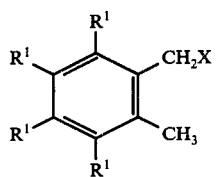

in which $R^1$ has the above meanings and X is halogen, with a benzene of the formula

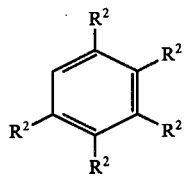

in which $R^2$ has the above meanings, in a two phase aqueous/organic reaction medium, wherein the organic phase is finely dispersed in the aqueous phase with droplets of the organic phase being at most 1,000 nanometers in size, and in the presence of sulfuric acid alone as the catalyst in a molar ratio of sulfuric acid to the starting material II of at least 3:1 while using a ratio of from 1 mole up to less than 6 moles of starting material III per mole of starting material II.

2. A process as claimed in claim 1, wherein the reaction is carried out with from 3 to 15 moles of sulfuric acid per mole of starting material II.

3. A process as claimed in claim 1, wherein the reaction is carried out with a volume ratio of from 0.5 to 2 parts by volume of organic phase per part by volume of aqueous phase in the reaction mixture.

4. A process as claimed in claim 1, wherein the reaction is carried out at from 40° to 160° C.

5. A process as claimed in claim 1, wherein the reaction is carried out at from 60° to 130° C.

6. A process as claimed in claim 1, wherein the reaction is carried out at from 75° to 90° C.

7. A process as claimed in claim 1, wherein the reaction is carried out in the presence of from 10 to 100 per cent by weight, based on starting material II, of a solvent which is inert under the reaction conditions.

8. A process as claimed in claim 1 wherein the reaction is carried out with a ratio of about 2 to 6 moles of starting material III per mole of starting material II.

9. A process as claimed in claim 1 wherein the reaction is carried out with a ratio of about 4 to 6 moles of starting material III per mole of starting material II.

10. A process as claimed in claim 1 wherein the reaction is carried out with concentrated sulfuric acid of from 50 to 100% strength by weight.

11. A process as claimed in claim 1 wherein the reaction is carried out with concentrated sulfuric acid of from 70 to 90% strength by weight.

12. A process as claimed in claim 1 wherein the reaction is carried out with sulfuric acid of from 78 to 82% strength by weight and in an amount of from about 3 to 6 moles of sulfuric acid, expressed as 100% strength, per mole of starting material II.

13. A process as claimed in claim 1 wherein the starting materials II and III are selected wherein:

$R^1$ is hydrogen, chlorine or bromine;

$R^2$ is hydrogen, chlorine, bromine, alkyl of 1 to 6 carbon atoms, phenyl or phenyl substituted by alkyl of 1 to 4 carbon atoms; and X is bromine or chlorine.

* * * * *